US012700085B2

(12) United States Patent
MacKinnon

(10) Patent No.: US 12,700,085 B2
(45) Date of Patent: Aug. 4, 2026

(54) MEDICAL INFORMATION PROCESSING SYSTEM AND METHOD

(71) Applicant: Canon Kabushiki Kaisha, Tokyo (JP)

(72) Inventor: Hamish Iain MacKinnon, Edinburgh (GB)

(73) Assignee: Canon Kabushiki Kaisha, Tokyo (JP)

( * ) Notice: Subject to any disclaimer, the term of this patent is extended or adjusted under 35 U.S.C. 154(b) by 503 days.

(21) Appl. No.: 17/980,917

(22) Filed: Nov. 4, 2022

(65) Prior Publication Data

US 2024/0153072 A1 May 9, 2024

(51) Int. Cl.
*G06F 16/36* (2019.01)
*G06N 5/02* (2023.01)
*G06T 7/00* (2017.01)
*G06T 7/10* (2017.01)
*G06V 10/74* (2022.01)
*G16H 30/20* (2018.01)

(52) U.S. Cl.
CPC .......... *G06T 7/0012* (2013.01); *G06F 16/367* (2019.01); *G06N 5/02* (2013.01); *G06T 7/10* (2017.01); *G06V 10/761* (2022.01); *G16H 30/20* (2018.01); *G06T 2207/20104* (2013.01)

(58) Field of Classification Search
CPC ..................... G06T 7/0012; G06T 7/10; G06T 2207/20104; G16H 30/20; G06F 16/367; G06V 10/761; G06N 5/02
USPC ......................................... 382/128, 190, 195
See application file for complete search history.

(56) References Cited

U.S. PATENT DOCUMENTS

| | | | |
|---|---|---|---|
| 2008/0027917 A1 | 1/2008 | Mukherjee et al. | |
| 2009/0070103 A1* | 3/2009 | Beggelman | G06F 40/20 704/9 |
| 2010/0172567 A1 | 7/2010 | Prokoski | |
| 2010/0189320 A1 | 7/2010 | Dewaele | |
| 2011/0087670 A1 | 4/2011 | Jorstad et al. | |
| 2011/0317892 A1 | 12/2011 | Greenspan et al. | |
| 2012/0014559 A1 | 1/2012 | Suehling et al. | |
| 2012/0020536 A1* | 1/2012 | Moehrle | G06T 7/0014 382/128 |
| 2013/0036111 A2* | 2/2013 | Kramer | G06F 16/532 707/723 |

(Continued)

FOREIGN PATENT DOCUMENTS

| | | |
|---|---|---|
| CN | 106940728 A | 7/2017 |
| CN | 107247881 A | 10/2017 |
| EP | 3 567 525 A1 | 11/2019 |

OTHER PUBLICATIONS

"Medical Devices, Clinical decision support solutions" https://contextflow.com/solutions/medical-devices/ (3 pages).

(Continued)

*Primary Examiner* — Jamares Q Washington
(74) *Attorney, Agent, or Firm* — Oblon, McClelland, Maier & Neustadt, L.L.P.

(57) ABSTRACT

A medical information processing system comprises: a data store storing a medical ontology, knowledge graph or other knowledge base; and processing circuitry configured to: receive medical image data; receive an input regarding position on the medical image data; specify a concept in the medical ontology, knowledge graph or other knowledge base which includes or is related to the position; and specify text data including a term included in or related to the specified concept.

16 Claims, 3 Drawing Sheets

(56) References Cited

U.S. PATENT DOCUMENTS

| 2013/0251233 | A1 | 9/2013 | Yang et al. | |
| 2013/0275429 | A1* | 10/2013 | York | G06F 16/435 |
| | | | | 707/E17.002 |
| 2014/0254906 | A1 | 9/2014 | Poole et al. | |
| 2015/0161786 | A1 | 6/2015 | Seifert | |
| 2015/0331929 | A1 | 11/2015 | El-Saban et al. | |
| 2016/0063720 | A1 | 3/2016 | Han et al. | |
| 2016/0092748 | A1 | 3/2016 | Koktava et al. | |
| 2016/0155236 | A1 | 6/2016 | Davey | |
| 2018/0268548 | A1 | 9/2018 | Lin et al. | |
| 2019/0188848 | A1 | 6/2019 | Madani et al. | |
| 2020/0258233 | A1 | 8/2020 | Kruecker et al. | |
| 2021/0183487 | A1 | 6/2021 | Teodoro et al. | |
| 2022/0067074 | A1 | 3/2022 | O'Neil et al. | |

OTHER PUBLICATIONS

Li, X. et al. "Oscar: Object-Semantics Aligned Pre-training for Vision-Language Tasks" CoRR abs/2004.06165 (2020) https://arxiv.org/pdf/2004.06165y6.pdf (21 pages).
Dabbah, M. et al. "Detection and location of 127 anatomical landmarks in diverse CT datasets" SPIE Medical Imaging, vol. 9034, 2014. (12 pages).

* cited by examiner

MEDICAL INFORMATION PROCESSING SYSTEM AND METHOD

FIELD

Embodiments described herein relate generally to a medical information processing system and method, for example a system and method for searching a medical image based on a text input, or for searching text based on an input related to a medical image.

BACKGROUND

It is known to produce medical images from medical image data that is obtained by scanning a region of a patient or other subject using any suitable medical imaging modality.

Reading medical images may typically be hard and time consuming. Reading medical images may be hard for non-specialists and time-consuming for experts even when an accurate radiology report is provided.

Searching within medical images barely exists. Users typically have to manually scroll and control to show relevant data. With regard to control, for example, medical images are often captured at a high contrast resolution—for example data of CT scans can have values up to thousands of Hounsfield Units, or may have negative or fractional values. In contrast, computer screens are usually engineered to handle only 255 values of contrast, so users see a window of the full contrast, which is adjusted by for example changing the window midpoint level or the width across the HU scale. Body parts may be either clearly visible or completely invisible in the same slice of data depending on how midpoint levels or widths, or other parameters, are set.

After looking at an image of a patient, a user may wish to find out whether there are previous relevant references in the patient's health record. Typically, looking for previous references in the health record requires either manually looking for the references or stopping to think of search terms that are likely to be useful in searching the health record.

BRIEF DESCRIPTION OF THE DRAWINGS

Embodiments are now described, by way of non-limiting example, and are illustrated in the following figures, in which.

DETAILED DESCRIPTION

Certain embodiments provide a medical information processing system comprising: a data store storing a medical ontology, knowledge graph or other knowledge base; and processing circuitry configured to: receive medical image data; receive an input regarding position on the medical image data; specify a concept in the medical ontology, knowledge graph or other knowledge base which includes or is related to the position; and specify text data including a term included in or related to the specified concept.

Certain embodiments provide a medical information processing method comprising: receiving medical image data; receiving an input regarding position on the medical image data; specifying a concept in a medical ontology, knowledge graph or other knowledge base which includes or is related to the position; and specifying text data including a term included in or related to the specified concept.

Certain embodiments provide a medical information processing system comprising: a data store storing a medical ontology, knowledge graph or other knowledge base; and processing circuitry configured to: receive a text query and medical image data; specify a node of the medical ontology, knowledge graph or other knowledge base based on the text query; specify anatomical information based on a concept corresponding to the specified node; and specify a point or region on the medical image data corresponding to the specified anatomical information.

Certain embodiments provide a medical information processing method comprising: receiving a text query and medical image data; specifying a node of a medical ontology, knowledge graph or other knowledge base based on the text query; specifying anatomical information based on a concept corresponding to the specified node; and specifying a point or region on the medical image data corresponding to the specified anatomical information.

Figure 1:
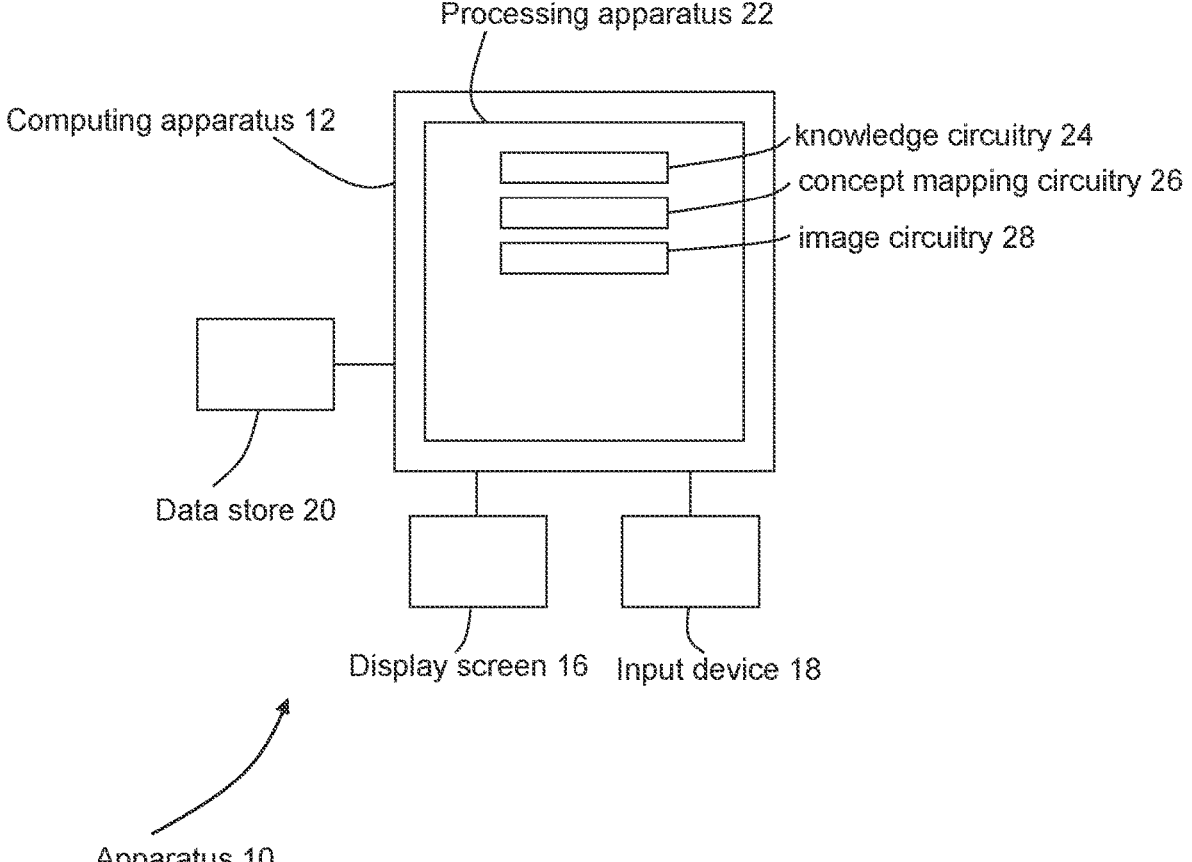
FIG. 1 is a schematic diagram of an apparatus according to an embodiment.

An apparatus 10 according to an embodiment is illustrated schematically in FIG. 1. The apparatus 10 may also be referred to as a medical information processing system. In the present embodiment, the apparatus 10 is configured to process medical data, for example Electronic Medical Records. The medical data may comprise both image data and text data. The text data may comprise free text data such as clinical notes or letters. The image data may comprise data representative of images acquired by performing medical imaging scans in any appropriate medical imaging modality, for example magnetic resonance (MR), computed tomography (CT), cone-beam CT, positron emission tomography (PET), X-ray, or ultrasound.

In other embodiments, the apparatus 10 may be configured to process any appropriate data, which may comprise non-medical data.

For instance, in some embodiments, the apparatus 10 may be configured to process genetic data or other non-imaging data. In some embodiments, landmarks are genes or gene clusters in a genome or transcriptome and the ontology, knowledge graph or other knowledge base may describe metabolic links or other parameters. In another embodiments, the apparatus may be configured to search or otherwise process a film or other audio-visual data, for instance to identify each instance of a particular object appearing. The apparatus 10 may be used for any other suitable applications.

The apparatus 10 comprises a computing apparatus 12, which in this case is a personal computer (PC) or workstation. The computing apparatus 12 is connected to a display screen 16 or other display device, and an input device or devices 18, such as a computer keyboard and mouse.

The computing apparatus 12 receives medical data from a data store 20, which may also be referred to as a memory or as storage. In alternative embodiments, computing apparatus 12 receives medical data from one or more further data stores (not shown) instead of or in addition to data store 20. For example, the computing apparatus 12 may receive medical data from one or more remote data stores (not shown) which may form part of an Electronic Medical Records system or Picture Archiving and Communication System (PACS), or which may comprise cloud-based storage.

The data store 20 further stores a medical ontology which is based on medical knowledge. In the present embodiment, the medical ontology comprises a knowledge graph comprising information from UMLS (Unified Medical Language System). The medical ontology comprises knowledge about a large number of medical concepts and their relationships. In other embodiments, the medical ontology may be stored in any suitable memory, for example in another apparatus or in a cloud-based memory.

In other embodiments, a knowledge graph or any other suitable knowledge base may be used instead of a medical ontology. The knowledge base may, for example, be structured according to a medical ontology.

In the embodiment of FIG. 1, the data store 20 further stores a bidirectional mapping function which relates medical concepts of the medical ontology to anatomical points or regions, for example anatomical landmarks. In other embodiments, the bidirectional mapping function may be stored in any suitable memory, for example in another apparatus or in a cloud-based memory.

Computing apparatus 12 is configured to receive information from the medical ontology and from the bidirectional mapping function.

Computing apparatus 12 provides a processing resource for automatically or semi-automatically processing medical text data. Computing apparatus 12 comprises a processing apparatus 22. The processing apparatus 22 comprises knowledge circuitry 24 which is configured to link text to medical concepts in the medical ontology; concept mapping circuitry 26 which is configured to map medical concepts to anatomical points or regions using the bidirectional mapping function; and image circuitry 28 which is configured to locate anatomical points or regions within medical image data.

In the present embodiment, the circuitries 24, 26, 28 are each implemented in computing apparatus 12 by means of a computer program having computer-readable instructions that are executable to perform the method of the embodiment. However, in other embodiments, the various circuitries may be implemented as one or more ASICs (application specific integrated circuits) or FPGAs (field programmable gate arrays). Functionality of one or more of the circuitries may be implemented in one or more cloud-based computing resources.

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
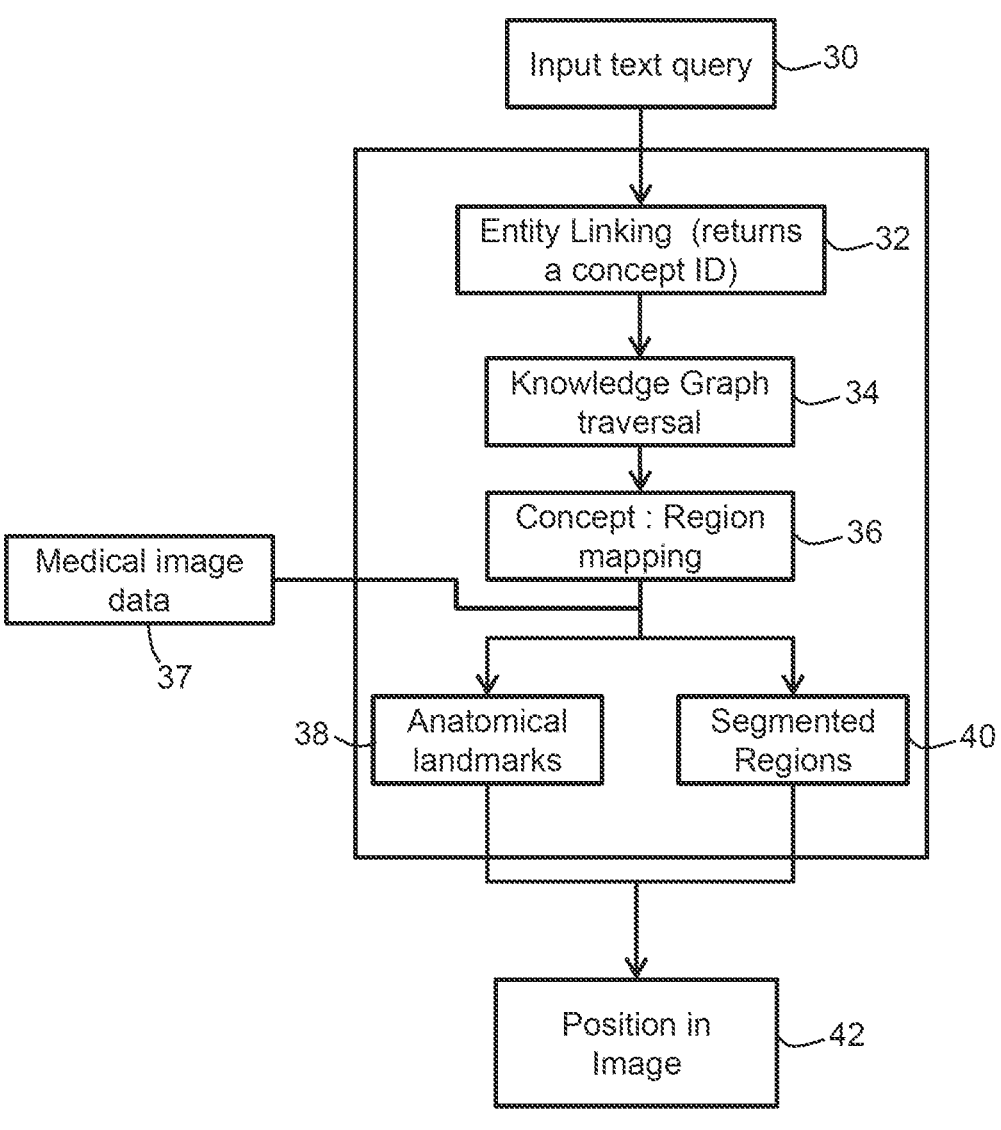
FIG. 2 is a flow chart illustrating in overview a method in accordance with an embodiment.

FIG. 2 is a flow chart illustrating in overview a method for using text to search medical images. The method of FIG. 2 uses pixel data content of medical images to search the medical images. In the method of FIG. 2, anatomical landmarks are identified based on text input. In other embodiments, any suitable anatomical points or regions may be identified. The method of FIG. 2 provides a multimodal search method in which a query in a text modality is used to search medical image data, which is data of a different modality.

At stage 30, a clinical user, for example a physician, inputs a text query. In other embodiments, the text query may be input by any suitable user, for example any suitable medical professional or researcher.

The text query may also be described as a search term or search input. The text query may comprise a word, a plurality of words, a part of a word, an abbreviation or acronym, or any other suitable text input. The text query may be described as free text input. The text query may not be limited to a list of terms or to a limited vocabulary.

In the embodiment of FIG. 2, the text query is manually input using input device 18, which may comprise, for example, a keyboard, mouse or touch screen. For example, the text query may be typed into a text box on a user interface displayed on display screen 16.

In other embodiments, any suitable type of user input may be used, where user input is input provided by a user rather than by the system itself. The user input may comprise manual selection from a list or menu. In some embodiments, the user input is provided using a hands-free method, which may also be described as a hands-off method. For example, the user input may be provided by eye tracking, gaze tracking, voice recognition, gesture control or hand tracking. Using a hands-off input method may provide greater ease and flexibility of input for the user.

In further embodiments, a text query may be automatically selected by the knowledge circuitry 24. For instance, in one specific example, text used as a query could be the output of a system that automatically selects relevant details from a document, e.g. a system for stroke reports might automatically select mentions of ischaemia or haemorrhage, and as a follow up might be able to extract positional information about this too (like " . . . haemorrhage in left temporal lobe . . . " leads to "left temporal lobe" as a query).

The knowledge circuitry 24 receives the text query that has been input by the user.

At stage 32, the knowledge circuitry 24 performs an entity linking procedure which associates the text query with one or more concepts in a medical ontology.

The medical ontology is stored in the data store 20. In other embodiments, the medical ontology may be stored in any suitable data store.

In the present embodiment, the medical ontology is a knowledge graph comprising information from UMLS (Unified Medical Language System). In other embodiments, any suitable knowledge base may be used to store information about concepts and their relationships, for example any suitable database, knowledge graph or ontology. In some embodiments, a different concept space may be used, which may not be UMLS.

The knowledge graph comprises a plurality of nodes, each of which is representative of a respective concept having a corresponding concept unique identifier (GUI). The nodes are connected by edges. Each edge is representative of a relationship between the two nodes that it connects. Many different relationships may be represented by different edges of the knowledge graph. For example, a relationship between nodes may be is_a, inverse_isa, has_member, has_part, may_treat, cause_of, associated_symptom_of, or any suitable relationship The knowledge graph may be considered to be representative of a concept space in which related concepts are closer together (for example, connected by a lower number of edges) than unrelated concepts.

Each concept may be expressed by multiple different words or phrases, which may be described as surface forms. For example, one node in the knowledge graph is representative of UMLS concept C0000970. Concept C0000970 includes the surface forms 'acetaminophen', 'acetamidophenor', 'acetominophen', 'hydroxyacetanilide', 'paracetamol', 'paracetamol', 'paracetamol product', 'acmp', 'apap', 'acetaminofen', 'paracetamolum', 'acenor', 'analgesics acetaminophen', ''アセトアミノフェン''. All of these surface forms have equivalent meanings. They are specific synonyms to each other.

Therefore, each of the nodes in the knowledge graph is representative of a respective single concept, but may typically store more than one surface form for that concept.

The entity linking procedure comprises using the text query to specify at least one node and returning the concept(s) associated with the specified node(s). Each concept is identified by a respective concept unique identifier (CUI).

In some circumstances, a text query may be mapped directly to a concept in the knowledge graph. For example a text query comprising the text 'myocardial infarction' may be mapped directly to the concept of myocardial infarction in UMLS. In other circumstances, the exact text of the text query may not be present in UMLS. The mapping of the text query onto the knowledge graph may be based at least in part on at least one of: fuzzy matching using an edit distance such as a Levenshtein edit distance; phonetic matching using a matching algorithm, for example Metaphone; stemming; and/or dictionary look-up of abbreviations. The text query may be mapped to the knowledge graph by using a similarity between word embeddings for the text query and for one or more words within the knowledge graph. In other embodiments, any suitable technique may be used to map the text query to the knowledge graph.

In some embodiments, the mapping of the text query onto the knowledge graph comprises determining a distance between the text query and one or more potentially relevant text terms in the knowledge graph. For example, the distance may be a similarity which is obtained using word embeddings. The distance may be used in ranking or filtering potentially relevant text terms in order to map the text query to one or more concepts within the knowledge graph.

At stage 34, the knowledge circuitry 24 uses a semantic search function to expand the concept(s) associated with the text query to related terms. The semantic search function may also expand the concept(s) associated with the text query to related nodes.

Some methods of expanding to related terms are knowledge agnostic and can be applied before or after (or without) using the or a ontology, knowledge graph or other knowledge base.

For example, one method of accounting for misspellings in documents being searched is to create an index of all the words that are used in the document. If any of these words is a single character different from expansion candidates, this (probably misspelled) word may be included as an expansion also.

The semantic search function is configured to receive an input term and to produce a set of related terms for the input terms. For example, the semantic search function may receive the term 'edema' and determine a list of terms that are related to edema, which includes the terms 'hypertension', 'hydrochlorothiazide', 'chest pain', 'shortness of breath', 'swelling', 'dizziness', 'extremities', 'facial' and 'vascular'. The list of related terms also includes the original search term 'edema'.

The related terms may comprise alternative surface forms for the concept(s) identified at stage 32 and/or surface forms for concepts that are related to the concept(s) identified at stage 32.

The semantic search function may determine the related terms based at least in part on the medical ontology. Additionally or alternatively, the semantic search function may determine related terms based at least in part on at least one of: fuzzy matching using an edit distance such as a Levenshtein edit distance; phonetic matching using a matching algorithm, for example Metaphone; word embeddings;

stemming; and/or dictionary look-up of abbreviations. A machine learning model may be used to determine the related terms, for example a model as described in U.S. patent application Ser. No. 17/011,363, which is hereby incorporated by reference.

Expansion of a concept to related concepts may comprise traversing the knowledge graph according to predefined traversal rules. The original concept(s) associated with the text query may be referred to as a starting concept(s). In some circumstances, the traversal may be informed by features of the starting concept.

The semantic search function may expand a concept to its hyponyms, which are concepts that are contained within, and more specific than, the concept. The hyponyms may also be described as child concepts.

The semantic search function may traverse the knowledge graph using conditioned linking of concepts. For example, the semantic search function may use is_a relationships between nodes to determine that warfarin is_a haematological agent is_a medication.

The semantic search function may limit a traversal to stay within a given category or categories. For example, if the starting concept is a medication, the semantic search function may only expand to related concepts that are themselves medications. A concept of a medication may not be expanded to a disease associated with that medication.

Traversal rules may be dependent on a semantic type of the starting concept, such that different traversal rules are applied to starting concepts of different semantic types. For example, different traversal rules may be applied to a medication than to a disease.

Traversal rules may be informed by distance in the graph, for example a number of relationships (edges). For example, traversal may cease after a predetermined number of edges. Distance in the knowledge graph may be used to rank concepts. For example, a predetermined number of concepts may be returned based on the ranking, such as for example the top 5 concepts. Distance in the knowledge graph may be used to filter concepts. For example, only concepts that are within a predetermined distance from the starting concept may be returned. In some embodiments, the pre-determined distance may be set by the user.

Traversal rules may be dependent on a node level of the starting concept, such that different traversal rules are applied to starting concepts having different node levels. For example, the hypernyms (i.e., parent concepts) of a high-level node are usually not closely related terms. Therefore in some embodiments navigation through the knowledge graph would omit upward is_a relationships if the starting concept is a high-level node.

Traversal rules may be informed by a sequence of relationship traversals. For example, for a medication, if the has_active_ingredient edge is followed, then a subsequent traversal may omit active_ingredient_of edges. For instance, the medication co-codamol contains both paracetamol and codeine. If co-codamol is searched for, then paracetamol is a relevant finding. However, Lemsip (for which paracetamol is also an active ingredient) would not be a relevant finding in relation to co-codamol.

Traversal rules from a given node may be dependent on a connectivity of that node, where a number of edges connected to a node denotes its connectivity.

In other embodiments, any suitable traversal rules may be used to traverse the knowledge graph or other knowledge base.

In some embodiments, the semantic search function may traverse the knowledge graph from the starting concept until one or more concepts that are representative of anatomy are found in the knowledge graph. The semantic search function may rank concepts that are representative of anatomy in dependence on their distance from the starting concept, for example where distance is expressed in a number of edges. The semantic search function may filter concepts that are representative of anatomy to include only concepts that are within a predetermined distance from the starting concept, for example within a predetermined number of edges.

In the present embodiment, the semantic search function outputs a set of related terms and a set of concepts at the end of stage 34. The set of concepts includes any concept identified at stage 32 and any related concept identified at stage 34. In some embodiments, each of the related terms and/or concepts may have an associated relevance score, for example to rank the related terms and/or concepts by how relevant each related term and/or concept is considered to be.

In other embodiments, the knowledge circuitry 24 may determine and/or output concepts at stage 34 without also determining and/or outputting a set of related terms.

In many embodiments, searching for related concepts will give related terms. For example, terms may be all connected to a specific concept with the exception of knowledge-agnostic methods (e.g. spelling corrections of typed terms) but there are generally relatively few knowledge-agnostic methods and in some examples these may in practice give the same set anyway.

At stage 36, the concept mapping circuitry 26 connects the set of concepts to one or more anatomical regions. The anatomical regions in stage 36 are defined in a general or conceptual sense and not in relation to a specific human subject. Each anatomical region may comprise at least one anatomical landmark and/or at least one anatomical volume.

The concept mapping circuitry 26 may transfer relevance scores for each of the concepts to the anatomical regions, or may modify the relevance scores. The anatomical regions may be ranked by relevance.

In the embodiment of FIG. 2, the connecting of the set of concepts to one or more anatomical regions comprises using a bidirectional mapping function to connect each concept of the set of concepts to a respective one or more anatomical concepts, for example by traversing connections between nodes of the knowledge graph to nodes of a further ontology as described below. For example, the concept mapping circuitry 26 may traverse connections to determine which anatomical landmark or other anatomical region is closest to each of the concepts of the set of concepts. The concept mapping circuitry 26 may rank and/or filter anatomical regions based on a distance from a concept, for example a number of edges. In other embodiments, any suitable mapping method may be used to connect the set of concepts to one or more anatomical regions.

In the embodiment of FIG. 2, the bidirectional mapping function is stored in the data store 20. The bidirectional mapping function provides a mapping between concepts in the knowledge graph and anatomical regions, for example anatomical landmarks.

An anatomical landmark is usually a well-defined point in an anatomy, which in the present embodiment is the human anatomy. Anatomical landmarks may be defined in relation to anatomical structure such as bones, vessels or organs. For example, in one known method, 22 head landmarks and 100 thorax landmarks are defined.

Examples of anatomical landmarks include the center of the right eye and the apex of the right lung. The anatomical definition of a given landmark may be used to locate that landmark in many different medical imaging data sets. For example, if the center of the right eye is determined as an anatomical landmark, the landmark at the center of the right eye may be located in any medical imaging data set in which the center of the right eye is present, by any manual or automatic method that can locate that point in the anatomy.

The anatomical definition of each anatomical landmark is pre-determined by clinical experts, and each landmark has a clear identity. Anatomical landmarks may be defined anatomically on a generic human body.

In the embodiment of FIG. 2, the bidirectional mapping function comprises a further ontology, which in the embodiment of FIG. 2 is a further knowledge graph. The further ontology may comprise information that goes beyond the information that is contained in the knowledge graph that was used in stage 36. The further ontology may include information that is not included in UMLS. Some anatomical knowledge may not be included in UMLS. For example, some anatomical landmarks may not have corresponding UMLS concepts. Some anatomical links or relationship may not be included in UMLS.

In the embodiment of FIG. 2, the further ontology of the bidirectional mapping function comprises nodes that are additional to the nodes provided in the UMLS knowledge graph. The further ontology may include nodes that are representative of each of a plurality of anatomical landmarks. For example, a node may be defined for a concept of 'opisthion anatomical landmark' that is separate from the UMLS concept C1184889, 'opisthion', 'foramen magnum opisthion'.

The further ontology may further comprise nodes that are representative of anatomical regions, for example anatomical landmark regions, which are volumes instead of single points. For example, a node may be defined for a concept of 'foramen magnum anatomical landmark region', where the foramen magnum is the space between the opisthion and the basion, which is the space for the brain stem.

An anatomical region may comprise an anatomical volume, which may be defined based on one or more anatomical landmarks.

In some embodiments, a space filling method may be used to produce an anatomical region around one or more anatomical landmarks. For example, the space filling method may comprise a Voronoi method. In some embodiments, an anatomical atlas may be used to define an anatomical region. In some embodiments, a segmentation method for a defined concept may be used to define an anatomical region.

A node of the further ontology of the bidirectional mapping may be connected with other nodes of the further ontology. For example, an anatomical region may be connected to one or more anatomical landmarks.

The bidirectional mapping function includes predetermined mappings between nodes in the bidirectional mapping function and nodes in the knowledge graph, which in the embodiment of FIG. 2 is a UM LS knowledge graph.

Some anatomical landmarks map directly to anatomical concepts in UMLS with a one to one mapping. For example, in one known set of anatomical landmarks, the pineal gland is an anatomical landmark. There is a concept of pineal gland in UMLS. Therefore, a node in the bidirectional mapping function that is representative of the concept of pineal gland landmark may be mapped to the UMLS concept of pineal gland. The mapping is bidirectional, so the concept of the pineal gland is mapped to the concept of pineal gland landmark in the further ontology.

Some concepts in UMLS relate to multiple landmarks. The bidirectional mapping function includes predetermined mappings in which more than one anatomical landmark or region may map to a single concept in UMLS. For example, the head comprises multiple anatomical landmarks. In one known set of anatomical landmarks, the human head comprises 22 anatomical landmarks. The bidirectional mapping function may include a mapping from the concept of head to the 22 anatomical landmarks within the head. A plurality of anatomical landmarks may therefore be aggregated to match higher level concepts.

Conversely, the bidirectional mapping function may map a single anatomical landmark to more than one concept in UMLS.

Anatomical regions may occur between landmarks. In the embodiment of FIG. 2, the bidirectional mapping function includes mapping of concepts onto spaces between landmarks. Consider a text query that comprises the text 'Left temporal lobe'. At stage 32, the knowledge circuitry 24 maps the text query 'Left temporal lobe' onto a node representing the UMLS concept C0228233 which has the surface forms 'left temporal lobe', 'left lobe temporal'. At stage 36, the bidirectional mapping function maps the concept of left temporal lobe into a space between two known landmarks. Top of left ear and left lateral ventricle are known landmarks in head. The bidirectional mapping function identifies a region that is to the right of the top of left ear landmark and to the left of the left lateral ventricle landmark, and maps UMLS concept C0228233 to the identified region.

Some disease concepts may have an associated_location relationship that links them to an anatomical concept. The associated_location relationship may be used in determining a link between a disease concept and an anatomical landmark or other anatomical region.

At least some of the mapping of concepts on to anatomical landmarks or anatomical regions such as spaces between landmarks in the bidirectional mapping function may have been manually defined by one or more clinical experts. For example, a clinical expert may provide an annotation to one or more medical images, atlases or other data sources which may provide information to be added to the bidirectional mapping function.

In the embodiment of FIG. 2, the bidirectional mapping function is a function that has previously constructed by clinical experts using a known set of anatomical landmarks, and then stored. In other embodiments, the bidirectional mapping function may be constructed automatically or semi-automatically, for example using part_of relationships that relate anatomy concepts.

In some embodiments, the bidirectional mapping function may be a simpler mapping function, for example a mapping function that does not include its own nodes. For example, the bidirectional mapping function may define nearest neighbour node in the knowledge graph for each of the anatomical landmarks or anatomical regions.

In the embodiment of FIG. 2, the bidirectional mapping function is designed to map UMLS concepts to anatomy, and to map anatomy to UMLS concepts. In other embodiments, stage 36 may use a mapping function that works in a single direction to map UMLS (or other) concepts to anatomy.

By adding its own anatomical information, for example in the form of nodes of a further ontology, the bidirectional mapping function of FIG. 2 may combine UMLS knowledge and image knowledge. Stronger connections may be provided between anatomical landmarks and UMLS surface forms. A graph search may be easy to tune. It may be easy to add new sources of information to the bidirectional mapping function in future, for example to add information from image analysis. Information from disease segmentation may be added in some embodiments. An effectiveness of searching may be improved by improving anatomy links.

At the end of stage 36, the concept mapping circuitry 26 outputs one or more anatomical regions that have been determined by mapping the set of concepts that was output at the end of stage 34 onto anatomical concepts using the bidirectional mapping function. The one or more anatomical regions that are output at the end of stage 36 are defined in abstract terms, for example with reference to a generalized human anatomy.

In the embodiment of FIG. 2, stages 32, 34 and 36 are described as separate stages. In other embodiments, at least part of stages 32, 34 and 36 may be combined into a single stage. For example, a single stage may traverse both the knowledge graph of stage 34 and the further ontology of stage 36.

At stage 37, the image circuitry 28 receives medical image data that is representative of at least part of a patient or other subject. The medical image data may have been obtained by medical imaging in any suitable imaging modality, for example MR, CT, cone-beam CT, PET, X-ray, or ultrasound. In other embodiments, the image circuitry 28 may receive the medical image data at any suitable stage in the method of FIG. 2. For example, the medical image data may be received before the text query of stage 30. In some embodiments, the user may input the text query with reference to the medical image data, for example to find a specific anatomy within the medical image data. In some embodiments, the medical image data may be retrieved automatically or semi-automatically, for example in response to the anatomical regions that are output in stage 36.

In the present embodiment, the medical image data comprises two-dimensional image data. The two-dimensional image data may have been obtained by performing a rendering process on volumetric imaging data obtained from a scanner. The two-dimensional image data comprises a respective data value for each of a plurality of pixels. The data values may be representative of a respective intensity and/or color for each of the plurality of pixels. In other embodiments, the medical image data may comprise volumetric image data. In some embodiments, the medical image data may comprise two-dimensional image data along with volumetric image data from which the two-dimensional image data was rendered. In some embodiments, the image circuitry 28 may receive volumetric image data and render a two-dimensional image data set using the volumetric image data.

At stage 38, the image circuitry 28 processes the medical image data to obtain a location of one or more anatomical landmarks within the medical image data. The image circuitry 28 may use any suitable method for locating anatomical landmarks within the medical image data. For example, in some embodiments the image circuitry 28 may use a method as described in M. Dabbah, S. Murphy, H. Pello, R. Courbon, E. Beveridge, S. Wiseman, D. Wyeth, and I. Poole, "Detection and location of 127 anatomical landmarks in diverse CT datasets" in SPIE Medical Imaging, vol. 9034, 2014, which is hereby incorporated by reference. In other embodiments, the locations of anatomical landmarks in the medical image data may be received along with the medical image data.

The image circuitry 28 uses the anatomical landmarks identified in the medical image data to map one or more anatomical regions identified at stage 36 onto the medical image data. For example, if the pineal gland was identified as an anatomical region and output at stage 36, the image circuitry 28 may locate the pineal gland in the medical image data using an anatomical landmark for the pineal gland that has been identified in the medical image data.

The mapping performed by the image circuitry 28 links a location that was defined in abstract terms at stage 36 onto a specific position in an image, where the image is representative of a patient or other subject. The position may comprise a location of an individual landmarks, or a region surrounding one or more landmarks, or a region between landmarks.

The mapping may comprise a simple link from an anatomical landmark concept to an anatomical landmark position which is defined in the medical image data. The mapping may comprise using a region definition which defines a region in relation to anatomical, for example a region definition as defined by the bidirectional mapping function. The mapping may comprise a registration process, or any other suitable mapping process.

In some embodiments, an anatomical region around or between landmarks may be defined at stage 36 and then mapped onto the medical image data at stage 38. In other embodiments, locations of individual landmarks may be determined in the medical image data at stage 38 and a region around or between the landmarks may then be determined in the medical image data. For example, a space filling method may be used to produce a region around one or more landmarks in the medical image data. The space filling method may comprise a Voronoi method.

The mapping may make use of relevance scores that have been determined or modified at an earlier stage of FIG. 2. For example, the mapping may make use of the relevance scores to identify the most relevant anatomical regions on the medical image data.

The mapping of stage 30 may comprise selecting anatomical regions that are relevant to the medical image data, or to a region of interest within the medical image data. For example, in some circumstances a user may select a region of interest, or zoom in so that only a region of interest is shown. The image circuitry 28 may use the region of interest to inform the mapping so that only anatomical regions (for example, anatomical landmarks) are shown. For example, if the image is zoomed, the image circuitry 28 may map only anatomical regions that are usefully visible within the zoomed image.

The image circuitry 28 may choose between different levels of abstraction using a selection of a region of interest, a zoom level, or other image parameters. For example, the set of concepts that were returned at stage 34 may include an individual anatomical landmark, a smaller anatomical structure relating to the landmark (for example, the eye) and a larger anatomical structure (for example, the head). The image circuitry 28 may choose whether to map the individual landmark, the smaller anatomical structure and/or the larger anatomical structure based on a zoom level. Relevance scores of different abstractions may be amplified or attenuated based on whether the different abstractions should be usefully visible or not.

In some embodiments, the mapping of the anatomical concept(s) onto the medical image data may comprise choosing between anatomical concepts, for example to resolve an ambiguity. The set of concepts that is output at the end of stage 34 and then mapped onto anatomical regions may comprise two or more alternative possible concepts. For example, the term ventricle may refer to both the heart and the brain. The mapping of the anatomical concept(s) onto the medical image data may comprise determining whether the medical image data is representative of the heart or of the brain, and selecting the anatomical concept accordingly. In another example, the image circuitry 28 may choose between a left and a right hand. In some embodiments, the mapping may be dependent on a distance in concept space and/or a distance in image space.

In some embodiments, text associated with the medical image data may be used in the mapping of the anatomical region(s) onto the medical image data. Medical image data may often include associated text, for example text related to findings in the medical image data or to the acquisition of the medical image data. The text associated with the medical image data may be used, for example, to decide between different possible mappings or to rank different possible mappings. In other embodiments, the text associated with the medical image data may be used in any appropriate stage of the method of FIG. 2, for example to inform the traversal of the knowledge graph.

At the end of stage 38, the image circuitry 28 outputs one or more positions in the medical image data that correspond to the one or more anatomical regions identified at stage 38. Each position may comprise a point or area in the medical image data. In some embodiments, the positions may be ranked, for example using a relevance score.

In the embodiment of FIG. 2, the image circuitry 28 performs stage 40 in addition to stage 38. At stage 40, the image circuitry 28 segments the medical image data to obtain one or more segmented regions. Any segmentation method for a defined concept may be used to map boundaries of a given anatomy. The boundaries produced by segmentation may be sharp and accurate.

In other embodiments, the medical image data received by the image circuitry 28 already includes segmentation data, and the image circuitry 28 does not perform segmentation.

The image circuitry 28 uses the segmented regions in the medical image data to map one or more anatomical regions identified at stage 36 onto the medical image data. For example, if the one or more anatomical regions identified at stage 36 include lungs, the image circuitry 28 may use a lung segmentation to locate the lungs within the medical image data. The image circuitry 28 may make use of relevance scores to rank different anatomical regions, or may use a region of interest, zoom level or other image parameter in a similar manner to that described above with reference to stage 38.

At the end of stage 40, the image circuitry 28 may output one or more positions in the medical image data that correspond to the one or more anatomical regions identified at stage 38. In some embodiments, the positions may be ranked, for example using a relevance score.

Stage 40 may provide an alternative or additional method to link a location that was defined in abstract terms at stage 36 onto a specific location in an image, where the image is representative of a patient or other subject.

In other embodiments, stage 38 or stage 40 may be omitted. For example, locations may be identified in the medical image data using anatomical landmarks only, or using segmentations only. In further embodiments, any suitable method may be used to map the abstract anatomical concepts that were identified at stage 36 onto medical image data that is representative of a patient or other subject. In some embodiments, an identified region in an anatomical atlas may be mapped onto the medical image data, for example by using an image registration method and/or by using manifolds to transform from one representation to another.

At stage 42, the image circuitry 28 provides to the user the positions in the medical image data that were determined at stage 38 and/or stage 40. The image circuitry 28 may highlight the one or more positions to the user in a medical image, for example a medical image that is displayed on display screen 16. For example, the image circuitry 28 may highlight the one or more positions using color, shading or outlining. The image circuitry 28 may highlight the one or more positions by labelling the one or more positions with appropriate text, for example text that is indicative of the anatomy at the one or more locations.

In summary, the method of FIG. 2 uses anatomical landmarks or other anatomical regions to retrieve relevant image positions for a searcher given a text input. Relevant image positions are found using semantic links in a UM LS ontology.

The method of FIG. 2 may provide a method for searching within medical images. Although the method of FIG. 2 is described above in relation to a single set of medical image data, the method may also be used to search multiple images. For example, the method of FIG. 2 may be used to search all medical images relating to a single patient. The images may be of different modalities. The method of FIG. 2 may be used to search medical images for a plurality of patients.

The method of FIG. 2 may provide a user with a straight-forward method for searching one or more medical images using a text input. The text input may be simple for the user to provide. The user may not be required to use exact terms from a pre-determined list of terms in their text input. Instead, semantic functionality may be used to map the user's input to concepts which are then mapped to anatomy and to one or more images. The method of FIG. 2 may make reading medical images easier for some users by highlighting or annotating the medical images to indicate a relevant anatomy. The user may be able to use fewer manual steps in obtaining desired information.

In the embodiment of FIG. 2, text input is used to obtain locations on medical images. In other embodiments, locations on medical images may be used to find relevant text information.

Figure 3:
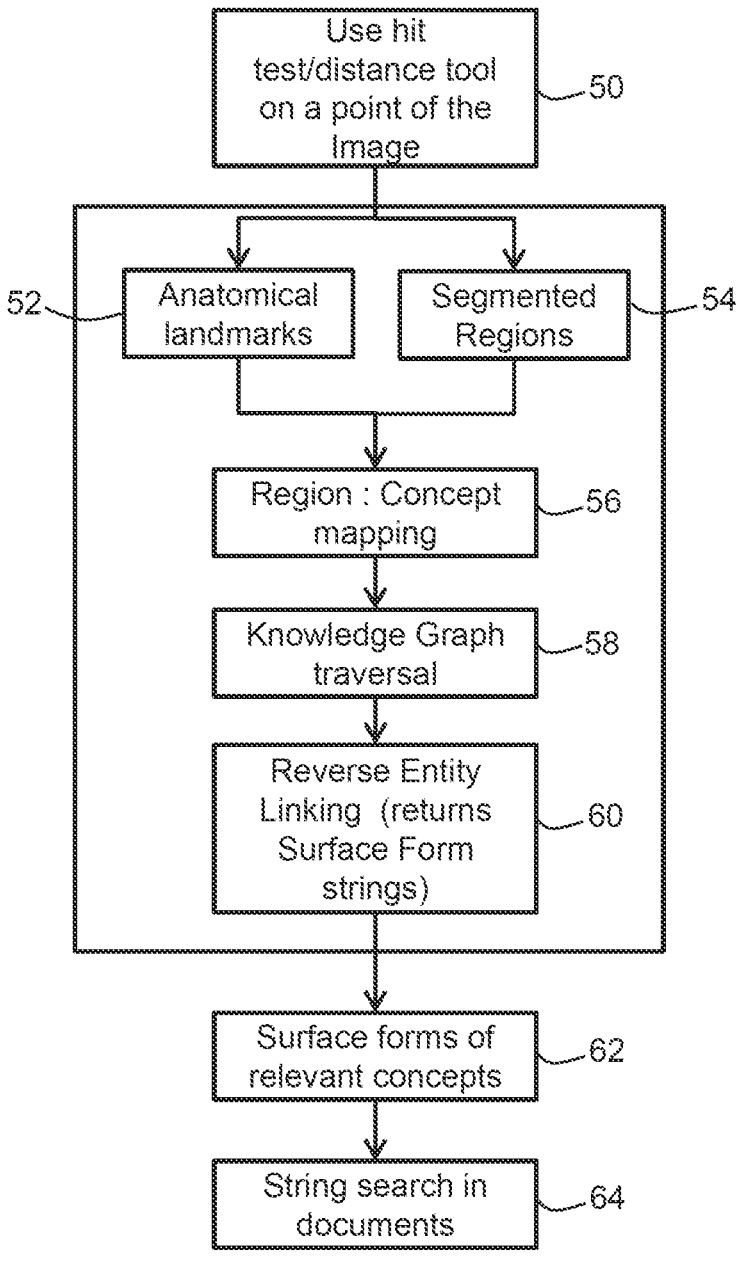
FIG. 3 is a flow chart illustrating in overview a method in accordance with an embodiment.

FIG. 3 is a flow chart illustrating in overview a method for searching text in dependence on an input provided on a medical image. The method of FIG. 3 uses image pixel data to search for related content in medical documents. The method of FIG. 3 uses anatomical landmarks which are identified in medical image data. An image space input may be used to retrieve relevant reports. The method of FIG. 2 provides a multimodal search method in which a query in an image modality is used to search text data, which is data of a different modality.

At stage 50, the image circuitry 28 receives medical image data that is representative of at least part of a patient or other subject. The medical image data may have been obtained by medical imaging in any suitable imaging modality, for example MR, CT, cone-beam CT, PET, X-ray, or ultrasound.

In the present embodiment, the medical image data comprises two-dimensional image data. The two-dimensional image data may have been obtained by performing a rendering process on volumetric imaging data obtained from a scanner. The two-dimensional image data comprises a respective data value for each of a plurality of pixels. The data values may be representative of a respective intensity and/or color for each of the plurality of pixels. In other embodiments, the medical image data may comprise volumetric image data. In some embodiments, the medical image data may comprise two-dimensional image data along with volumetric image data from which the two-dimensional image data was rendered. In some embodiments, the image circuitry 28 may receive volumetric image data and render a two-dimensional image data set using the volumetric image data.

The image circuitry 28 displays an image to the user. The image corresponds to, or is obtained from, the two-dimensional image data.

A clinical user, for example a physician, inputs an image query. The image query comprises a selection of a position in the displayed image. In other embodiments, the position may be selected by any suitable user, for example any suitable medical professional or researcher.

The selection of a position may comprise selecting a point or a region in the image. In some embodiments, the region may be the whole image.

In the embodiment of FIG. 2, the position is manually input using input device 18. For example, the input device 18 may comprise a mouse and the user may use the mouse to click on a point or to define a region, for example by clicking and dragging to define a bounding box. In other embodiments, any suitable type of user input may be used, where user input is input provided by a user rather than by the system itself. In some embodiments, the user input is provided using a hands-free method, which may also be described as a hands-off method. For example, the user input may be provided by eye tracking, gaze tracking, voice recognition, gesture control or hand tracking. Using a hands-off input method may provide greater ease and flexibility of input for the user.

A hit test may be used in some examples. A hit test can be a method available for use in tools for medical image viewers and similar (normally 3D) use cases in computer graphics. In 3D, when the user clicks on the screen, a ray is projected into the volume and checks each voxel it passes through. The voxel can be "empty" or "full"; the beam continues through empty voxels and stops on full ones. When the ray stops at the first "full" voxel, it has hit something and the position of this voxel is registered as the point that was hit. For 2D this simplifies to a single "inside or outside" check.

Once the hit point is found, then distance can be measured against other points e.g. landmarks.

One extension is that there can be more classes than just "full"—separate objects can have separate labels e.g. segmentations could be hit and return the segmentation label, like "heart".

The image circuitry 28 translates the user's input into one or more coordinates in a two-dimensional coordinate space of the displayed image, which may be described as an image space or as a slice space.

In other embodiments, any suitable method of determining one or more positions in image space may be used. In some embodiments, the one or more positions are determined automatically or semi-automatically, rather than being determined manually by a user.

In some embodiments, the selection of the position may be based on a user's selection of one or more imaging parameters, for example a viewing direction or zoom level. In some embodiments, the image space is a three-dimensional space and the user may provide an input that can be translated into three dimensional coordinates by the image circuitry 28. For example, the user may input commands to manipulate an image that is displayed, for example by rotation or zooming, and the image circuitry 28 may re-render and/or re-display a displayed image having different image parameters. The image circuitry 28 may use one or more image parameters requested by the user, for example a direction of view, to obtain coordinates in three-dimensional space.

At stage 52, the image circuitry 28 processes the medical image data to obtain a location of one or more anatomical landmarks within the medical image data. The image circuitry 28 may use any suitable method for locating anatomical landmarks within the medical image data. For example, in some embodiments the image circuitry 28 may use a method as described in M. Dabbah, S. Murphy, H. Pello, R. Courbon, E. Beveridge, S. Wiseman, D. Wyeth, and I. Poole, "Detection and location of 127 anatomical landmarks in diverse CT datasets" in SPIE Medical Imaging, vol. 9034, 2014. In other embodiments, the locations of landmarks in the medical image data may be received along with the medical image data.

The image circuitry 28 maps the position that was obtained from the user's input to one or more anatomical landmarks. For example, if the user has identified a region that includes only one anatomical landmark, the image circuitry 28 may map the user's region to the anatomical landmark. If the user has identified a region that includes more than one anatomical landmark, the image circuitry 28 may map the user's region to all included anatomical landmarks.

If the user has identified a point or region that does not directly include an anatomical landmark, the image circuitry 28 may maps the user's input to a nearest anatomical landmark, or to a predetermined number of nearest anatomical landmarks. The image circuitry 28 may determine a proximity of the identified point or region to one or more precomputed landmarks in the image. The proximity may be expressed as a distance. The image circuitry 28 may return one or more landmarks based on the proximity.

In some embodiments, the image circuitry 28 maps the position that is obtained from the user's input onto one or more predetermined anatomical regions, for example regions around or between landmarks.

At the end of stage 52, the image circuitry 28 returns data that is representative of one or more anatomical landmarks or other anatomical regions. In some embodiments, the image circuitry 28 may return a respective measure of distance from the selected position to each of a plurality of anatomical landmarks or other landmarks. The image circuitry 28 may rank the anatomical landmarks in order of distance. The image circuitry 28 may filter the anatomical landmarks based on distance, for example by discarding anatomical landmarks that are over a predetermined distance from the position selected by the user. In some embodiments, the predetermined distance may be selected by the user.

The image circuitry 28 may generate a relevance score that is indicative of the relevance of each of the anatomical landmarks or other anatomical regions that is returned. For example, the relevance score may be dependent on distance from the position obtained from the user input. In some embodiments, the image circuitry 28 may use a user's selection of a region of interest or a zoom level or another image parameters to obtain relevance scores for different anatomical regions, for example different anatomical landmarks. The relevance score may be amplified or attenuated based on whether the anatomical regions should be usefully visible or not. In some embodiments, anatomical regions of multiple levels of abstraction may be returned and the relevance score may amplify or attenuate relevance scores for different abstractions.

In the embodiment of FIG. 3, the image circuitry 28 performs stage 54 in addition to stage 52. At stage 54, the image circuitry 28 segments the medical image data to obtain one or more segmented regions. Any segmentation method for a defined concept may be used to map boundaries of a given anatomy. In other embodiments, the medical image data received by the image circuitry 28 already includes segmentation data, and the image circuitry 28 does not perform segmentation.

The image circuitry 28 uses the segmented regions in the medical image data to map the location obtained from the user's input to one or more anatomical regions. For example, the image circuitry 28 may identify that a region selected by the user includes the lungs based on a segmentation of the lungs. In some embodiments, the image circuitry 28 may return a respective measure of distance from the selected position to each of a plurality of segmented regions. The image circuitry 28 may rank the segmented regions in order of distance. The image circuitry 28 may filter the segmented regions based on distance, for example by discarding segmented regions that are over a predetermined distance from the position selected by the user. In some embodiments, the predetermined distance may be selected by the user. The image circuitry 28 may generate a relevance score that is indicative of the relevance of each of the anatomical landmarks or other anatomical regions that is returned. For example, the relevance score may be dependent on distance from the position obtained from the user input.

At the end of stage 54, the image circuitry 28 outputs data that is representative of one or more anatomical regions.

In other embodiments, stage 52 or stage 54 may be omitted. For example, the location provided by the user may be mapped using anatomical landmarks only, or mapped onto anatomical regions using segmentations only. In further embodiments, any suitable anatomical points or regions may be identified in the medical image data, and any suitable method may be used to map the position identified by the user onto anatomical concepts. For example, the position in the medical image data may be mapped onto an anatomical atlas, for example by using an image registration method.

At stage 56, the concept mapping circuitry 26 uses the bidirectional mapping function that was described above with reference to FIG. 2 to map anatomical regions that were obtained in stages 52 and/or 54 onto a medical ontology, for example to map anatomical landmarks onto the medical ontology. In the embodiment of FIG. 3, the medical ontology is a knowledge graph comprising information from UMLS as described above with reference to stage 32 of FIG. 2. In other embodiments, any suitable knowledge base may be used to store information about concepts and their relationships, for example any suitable database, knowledge graph or ontology. In some embodiments, a different concept space may be used, which may not be UMLS.

As described above with reference to stage 36 of FIG. 2, the bidirectional mapping function comprises a further ontology comprising nodes that are representative of anatomical landmarks or other anatomical regions, and includes a mapping between the nodes of the further ontology and nodes of the knowledge graph comprising information from UMLS. In other embodiments, any suitable mapping function may be used, which in some embodiments may not comprise nodes that are additional to those in the knowledge graph.

If the knowledge graph contains a node that corresponds directly to an anatomical landmark obtained in stage 52, the bidirectional mapping function may map that landmark to that node. For example, if a location identified by the user has been mapped to the pineal gland landmark at stage 52, the bidirectional mapping function maps the pineal gland landmark to the concept of pineal gland in the knowledge graph.

In some circumstances, the bidirectional mapping function may map multiple anatomical regions onto the same concept in the knowledge graph. In some circumstances, the bidirectional mapping function may map a single anatomical region onto multiple concepts in the knowledge graph. For example, the concepts may be of different levels of abstraction or different categories, or may comprise hyponyms or hypernyms.

At the end of stage 56, the concept mapping circuitry 26 outputs one or more concepts of the knowledge graph. Each concept is identified by a respective concept unique identifier (CUI).

The concept mapping circuitry 26 may generate, transfer or modify a respective relevance score for each of the concepts that it outputs. For example, the relevance score may be based on a distance determined at stage 54, or may rank concepts using their levels of abstraction.

At stage 58, the knowledge circuitry 24 uses a semantic search function to expand the concept(s) obtained in stage 56 to related terms. The semantic search function may also expand the concept(s) to related nodes. The semantic search function may be similar to that described above with reference to stage 34 of FIG. 2.

The semantic search function may determine the related terms based at least in part on the medical ontology. Additionally or alternatively, the semantic search function may determine related terms based at least in part on at least one of: fuzzy matching using an edit distance such as a Levenshtein edit distance; phonetic matching using a matching algorithm, for example Metaphone; stemming; and/or dictionary look-up of abbreviations. A machine learning model may be used to determine the related terms, for example a model as described in U.S. patent application Ser. No. 17/011,363, which is hereby incorporated by reference.

The semantic search function may traverse the knowledge graph using any suitable traversal rules, for example traversal rules as described above with reference to FIG. 2. The semantic search function may traverse the knowledge graph using conditioned linking of concepts. The semantic search function may use a distance within the knowledge graph to rank and/or filter concepts, for example by limiting distance to a predetermined distance, which may in some embodiments be selected by a user.

In some embodiments, text associated with the medical image data may be used in the traversal of the knowledge graph, or in any other appropriate stage of the method of FIG. 3. For example, text relating to findings in the medical image data may be used to rank and/or filter concepts, or to obtain a respective relevance score for each concept. In further embodiments, the user may input a text query in addition to the image query and information from the text query may be used in the traversal of the knowledge graph, or in any other appropriate stage of the method of FIG. 3.

At the end of stage 58, the knowledge circuitry 24 has obtained a set of related terms and a set of concepts. The set of concepts includes any concept identified at stage 56 and any related concept identified at stage 58. The knowledge circuitry 24 may generate, transfer or modify a respective relevance score for each of the related terms and/or concepts.

At stage 60, the knowledge circuitry 24 performs a reverse entity linking procedure which returns a respective set of surface forms for each concept of the set of concepts. The surface forms are returned as text strings.

At stage 62, the knowledge circuitry 24 outputs the surface forms for the set of concepts. In some embodiments, the knowledge circuitry 24 may display one or more of the surface forms to the user.

At stage 64, the knowledge circuitry 24 uses the surface forms to perform a string search for instances of the surface forms in a corpus of text, for example in one or more documents. For example, the documents may be clinical notes pertaining to the same patient as the medical image data obtained at stage 50. The documents may be documents that have been selected by the user. The knowledge circuitry 24 identifies any instances of any of the surface forms in the document(s). In some embodiments, the knowledge circuitry 24 may also search for related terms which are not included within the surface forms. In further embodiments, the knowledge circuitry 24 may search within any text data sources, for example documents, spreadsheets, test results or metadata text, for example metadata text accompanying medical images.

The knowledge circuitry 24 may display to the user the document(s), for example on display screen 16. Each may be displayed such that a portion of the document including one or more of the surface forms is on display. The surface forms may be highlighted in the document(s) in any suitable manner, for example by color, outlining, or any other suitable visual effect.

In other embodiments, the surface forms may be provided to any suitable further function, for example any suitable search function. In some embodiments, the surface forms and/or the instances of the surface forms in the documents may not be displayed to the user directly. In some embodiments, stage 64 may be omitted.

In one example, a user provides a location in an image using, for example, a mouse selection. The location is to the right of the anatomical landmark that is representative of the top of the left ear, and is to the left of the anatomical landmark that is representative of the left lateral ventricle. The concept mapping circuitry 26 maps a region to the right the top of the left ear and to the left of the left lateral ventricle to a UMLS concept C0228233 which has the surface forms 'left temporal lobe', 'left lobe temporal'. The knowledge circuitry 24 searches for the surface forms in a document and finds text data comprising the text "Irregularity in left temporal lobe . . . ". The knowledge circuitry 24 may then highlight this text to a user.

In some examples, a framework for a mouse cursor based tool can interact with a medical image based on the point that is clicked or clicked and dragged to perform some action. This might control zoom level, change the window width or window level for the densities displayed, allow text or line annotations, perform a hit test to select a segmentation, or perform any other suitable action.

The method of FIG. 3 may use landmarks to retrieve relevant reports for a user using an input in image space. Relevant text information may be found using semantic links in a UMLS ontology.

The method of FIG. 3 may provide a method of searching text based on an input relating to a medical image. Automatic text search functionality may be provided.

The method of FIG. 3 may provide a user with a straightforward method for searching one or more documents using an input provided on a medical image. It may be simple for the user to identify a point or region on a medical image. Semantic functionality may then be used to map the user's input to anatomy which are then mapped to concepts and to surface forms for the concepts. The surface forms may then be found in text data using known text methods.

The method of FIG. 3 may in some circumstances allow a user to find relevant references in a health record without having to manually search through documents, and without having to think of search terms that are likely to be useful.

The methods of FIG. 2 and/or FIG. 3 may benefit experienced users of radiology or PACS by speeding up a process of comparing images to notes or notes to prior images, which may lead to better user efficiency.

The methods of FIG. 2 and/or FIG. 3 may provide a method of training medical staff on unseen data. Existing training may require expert annotation to point out interesting and relevant features of medical images. By using a mapping from concepts to regions, information may be made available automatically on a novel scan without manual preparation. For example, anatomical labelling may be provided automatically, or a user may be able to click on an image to find out information about an anatomical region that they have clicked. The provision of such information may allow for easier training. A user who is not an expert on reading images or reports may be assisted in reading images or reports. Clicking on something in an image may take you to a text description. Inputting or selecting text may take you to a corresponding part of an image.

In some embodiments described above, a distance is used to rank or filter relevant returns, for example a distance in image space or in the concept space of the knowledge graph. In other embodiments, a distance in any suitable space (for example, slice space, image space, a latent concept space such as a space of word embeddings, or a concept space of a knowledge graph) may be used to rank and/or filter results. The use of a distance in an appropriate space to rank and/or filter returns may allow multiple search hits that are not themselves a direct match to be returned usefully. In further embodiments, distances described with reference to a particular embodiments above may be applied in any suitable embodiment. For example, distances described with reference to the embodiment of FIG. 2 may be applied to the embodiment of FIG. 3 or vice versa.

Features of FIG. 2 and features of FIG. 3 may be combined in any suitable combination. In some embodiments, one or more of the stages described above may be omitted, or multiple stages may be combined.

In the embodiments described above, the method of FIG. 2 and the method of FIG. 3 are both performed by the same circuitries of apparatus 10. In other embodiments, the method of FIG. 2 and the method of FIG. 3 may be performed on different apparatuses, or on any suitable combination of apparatuses. At least part of the method of FIG. 2 and/or FIG. 3 may be performed using a cloud-based resource.

In some above embodiments, information is obtained from an EHR relating to a patient. In other embodiments, a corresponding method may be performed on any suitable medical data for any human or animal subject. In further embodiments, a corresponding method may be performed using non-medical text data and image data.

Certain embodiments provide a medical information processing system comprising: a storage which stores medical ontologies, processing circuitry configured to: receive a text query and medical image data, receive an input regarding to position on the medical image data, specify a concept on the medical ontologies which include inputted position, specify text data including a term included in the concept.

Certain embodiments provide a medical information processing system comprising: a storage which stores medical ontologies, processing circuitry configured to: receive a text query and medical image data, specify a node on the medical ontologies based on the text query, specify a concept based on the node, specify anatomical information based on the specified concept, specify a region on the medical image data corresponding to the specified anatomical information.

Certain embodiments provide a computer method comprising: an image query defined as a manually or automatically selected point or region in an image; a mapping stating the image query in terms of proximity to precomputed landmarks in the image; a further mapping linking landmarks to concepts in an ontology; links from the concept of the ontology to relevant text terms using surface forms of the ontology, to produce the effect of relevant text retrieval for the given query.

The method may additionally comprise a method to use the distance (in slice-space, image-space, latent concept-space or knowledge graph edge distance) to rank and/or filter the relevant returns so that multiple search hits that are not themselves a direct match can be returned usefully where this distance parameter may optionally be configured by the user to change the result set.

The method may additionally comprise a device performing any or multiple of: eye tracking, gaze tracking, voice recognition, gesture control, hand tracking configured to select the image query to allow for hands-off operation.

The method may additionally comprise a method of aggregating landmarks to match higher level concepts from the ontology.

The method may additionally comprise a system matching the relevant text terms provided against a corpus of text (i.e. automatic text search functionality).

The method may additionally comprise a segmentation method to produce the image region or point used as a landmark.

The method may additionally comprise a method to use the findings attached to the image as a region to use as a landmark to influence the inclusion of text terms related to highlighted findings.

The method may additionally comprise a method to use the user interface's zoom level to amplify or attenuate the relevance score of different abstractions based on whether the sections should be usefully visible or not.

Certain embodiments provide a computer method comprising a text query defined as a manually or automatically selected string of text; a mapping linking the text query to concepts in an ontology; a further mapping concepts to an abstract definition of location in landmark space; a link from a location defined in abstract terms relative to landmark concepts to an image based on extracted landmarks that represent a point or region in an image, to produce the effect of image region retrieval for the given query.

The method may additionally comprise a method to use the distance (in slice-space, image-space, latent concept-space or knowledge graph edge distance) to rank and/or filter the relevant returns so that multiple search hits that are not themselves a direct match can be returned usefully where this distance parameter may optionally be configured by the user to change the result set.

The method may additionally comprise a device performing any or multiple of: eye tracking, gaze tracking, voice recognition, gesture control, hand tracking configured to select the text query to allow for hands-off operation.

The method may additionally comprise a method of aggregating landmarks to match higher level concepts from the ontology.

The method may additionally comprise a system matching the relevant text terms provided against a corpus of text (i.e. a query expansion system).

The method may additionally comprise a segmentation method to produce the image region or point used as a landmark.

The method may additionally comprise a method to include findings attached to the image when looking for nearby points of interest in the final connection to the image.

The method may additionally comprise a method to use the user interface's zoom level to amplify or attenuate the relevance score of different abstractions based on whether the sections should be usefully visible or not.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical information processing system comprising:
a data store storing a medical ontology, knowledge graph or other knowledge base; and
processing circuitry configured to:
  receive medical image data;
  receive an input regarding a position on the medical image data;
  use semantic functionality to map the input to at least one anatomical region;
  map the at least one anatomical region to a concept in the medical ontology, knowledge graph or other knowledge base which includes or is related to the position;
  determine at least one surface form for the concept;
  perform a semantic search, using the concept, in one or more pre-existing clinical notes or pre-existing health records for a patient that existed before the medical image data is received, the semantic search comprising:
    searching for the at least one surface form in text data of the one or more pre-existing clinical notes or pre-existing health records;
    identifying a portion of the one or more pre-existing clinical notes or pre-existing health records including the at least one surface form; and
    displaying the portion with the at least one surface form highlighted; and
  use a concept distance measure in a concept space of the medical ontology, knowledge graph or other knowledge base to rank and/or filter concepts and/or terms, wherein the concept space has nodes, each node representative of a concept,
  the nodes are connected by edges, each edge of the edges representative of a relationship between two nodes that the edge connects, and
  a result of the concept distance measure is expressed as a number of the edges.

2. A system according to claim 1, wherein the specified text data further comprises one or more synonyms and/or hyponyms for the specified concept.

3. A system according to claim 1, wherein the specifying of the concept comprises:
  determining based on the position and the medical image data at least one anatomical region; and
  mapping the at least one anatomical region to the medical ontology, knowledge graph or other knowledge base to obtain the specified concept.

4. A system according to claim 3, wherein the at least one anatomical region comprises at least one anatomical landmark.

5. A system according to claim 3, wherein the determining of the at least one anatomical region is dependent on a segmentation.

6. A system according to claim 3, wherein the specifying of the concept is based on a distance in image space from the position to the at least one anatomical region.

7. A system according to claim 1, wherein the receiving of the input regarding position comprises receiving user input that is representative of a selection of a point or region on the medical image data by a user.

8. A medical information processing method comprising:
  receiving medical image data;
  receiving an input regarding a position on the medical image data;
  using semantic functionality to map the input to at least one anatomical region;
  mapping the at least one anatomical region to a concept in a medical ontology, knowledge graph or other knowledge base which includes or is related to the position;
  determining at least one surface form for the concept;
  performing a semantic search, using the concept, in one or more pre-existing clinical notes or pre-existing health records for a patient that existed before the medical image data is received, the semantic search comprising:
    searching for the at least one surface form in text data of the one or more pre-existing clinical notes or pre-existing health records;
    identifying a portion of the one or more pre-existing clinical notes or pre-existing health records including the at least one surface form; and
    displaying the portion with the at least one surface form highlighted; and
  using a concept distance measure in a concept space of medical ontology, knowledge graph or other knowledge base to rank and/or filter concepts and/or terms, wherein
  the concept space has nodes, each node representative of a concept,
  the nodes are connected by edges, each edge of the edges representative of a relationship between two nodes that the edge connects, and
  a result of the concept distance measure is expressed as a number of the edges.

9. A medical information processing system comprising:
a data store storing a medical ontology, knowledge graph or other knowledge base; and processing circuitry configured to:

receive a text query and medical image data;

specify a node of the medical ontology, knowledge graph or other knowledge base based on the text query;

use semantic functionality to map a concept corresponding to the specified node and/or a related concept to at least one anatomical region;

specify a point or region on the medical image data corresponding to the at least one anatomical region;

determine at least one surface form for the concept;

perform a semantic search, using the concept, in one or more pre-existing clinical notes or pre-existing health records for a patient that existed before the medical image data is received, the semantic search comprising:

searching for the at least one surface form in text data of the one or more pre-existing clinical notes or pre-existing health records;

identifying a portion of the one or more pre-existing clinical notes or pre-existing health records including the at least one surface form; and displaying the portion with the at least one surface form highlighted; and use a concept distance measure in a concept space of the medical ontology, knowledge graph or other knowledge base to rank and/or filter concepts and/or terms, wherein the concept space has nodes, each node representative of a concept, the nodes are connected by edges, each edge of the edges representative of a relationship between two nodes that the edge connects, and a result of the concept distance measure is expressed as a number of the edges.

10. A system according to claim 9, wherein the processing circuitry is further configured to display an image based on the medical image data and to highlight the specified point or region on the displayed image.

11. A system according to claim 9, wherein the anatomical information comprises at least one anatomical landmark or anatomical region, and the specifying of the point or region on the medical image data comprises locating the at least one anatomical landmark or anatomical region in the medical image data.

12. A system according to claim 9, wherein the specifying of the anatomical information and/or the specifying of the point or region is dependent on a segmentation.

13. A system according to claim 9, wherein the specifying of anatomical information based on the concept corresponding to the specified node comprises obtaining at least one further concept or further term related to the specified node.

14. A system according to claim 9, wherein the specifying of the anatomical information comprises specifying anatomical information at different levels of generality.

15. A system according to claim 9, wherein the specifying of the anatomical information and/or specifying of the point or region is based on text information associated with the medical image data.

16. A medical information processing method comprising:

receiving a text query and medical image data;

specifying a node of a medical ontology, knowledge graph or other knowledge base based on the text query;

using semantic functionality to map a concept corresponding to the specified node and/or a related concept to at least one anatomical region;

specifying a point or region on the medical image data corresponding to the at least one anatomical region;

determining at least one surface form for the concept;

performing a semantic search, using the concept, in one or more pre-existing clinical notes or pre-existing health records for a patient that existed before the medical image data is received, the semantic search comprising:

searching for the at least one surface form in text data of the one or more pre-existing clinical notes or pre-existing health records;

identifying a portion of the one or more pre-existing clinical notes or pre-existing health records including the at least one surface form; and displaying the portion with the at least one surface form highlighted; and using a concept distance measure in a concept space of the medical ontology, knowledge graph or other knowledge base to rank and/or filter concepts and/or terms, wherein the concept space has nodes, each node representative of a concept, the nodes are connected by edges, each edge of the edges representative of a relationship between two nodes that the edge connects, and a result of the concept distance measure is expressed as a number of the edges.

* * * * *